United States Patent [19]
Davis

[11] 3,992,730
[45] Nov. 23, 1976

[54] SCRUB SINK
[76] Inventor: Edwin Dyer Davis, 330 Clyde Morris Blvd., Daytona Beach, Fla. 32014
[22] Filed: Dec. 2, 1975
[21] Appl. No.: 637,104

[52] U.S. Cl. .................................. 4/187 R; 4/166
[51] Int. Cl.² ..................................... A47C 19/00
[58] Field of Search ............... 4/1, 187 R, 166, 167, 4/168, 169, 188, 189, 190, 191, 192, 159

[56] References Cited
UNITED STATES PATENTS

| | | |
|---|---|---|
| 2,847,681 | 8/1958 | Jacobs .......................... 4/187 R |
| 3,298,037 | 1/1967 | Luthar ............................. 4/166 |
| 3,576,277 | 4/1971 | Blackmon ...................... 4/192 X |
| 3,728,745 | 4/1973 | Brandgord et al. ........... 4/187 R |

*Primary Examiner*—Henry K. Artis
*Attorney, Agent, or Firm*—Harold L. Stowell

[57] ABSTRACT

An anti-splash, non-contaminating scrub sink is provided wherein a zone in the bottom of the sink including the drain is perforate and a reduced pressure is maintained below the perforate zone to draw the scrub fluid from the sink. In one embodiment the perforate zone includes the entire bottom and a portion of the side walls of a liner for the sink.

5 Claims, 3 Drawing Figures

SCRUB SINK

BACKGROUND OF THE INVENTION

1. Field of the Invention

This invention relates to an improved scrub sink for use by doctors, nurses and other hospital personnel to scrub and clean their hands in pre-surgery and the like preparations.

2. Description of the Prior Art

Many improvements have been made in surgical scrub sinks such as automatic time and temperature controls to thereby provide the proper time and temperature for the flow of scrubbing fluid to the shower head of the sink. However, it has been found that a potential source of recontamination or cross-contamination exists by virtue of splash from the bottom and side walls of conventional scrub sinks.

It is therefore a primary object of this invention to provide a personnel scrub sink that eliminates or materially reduces scrub sink splash originating contamination.

SUMMARY OF THE INVENTION

The invention may be summarized as a personnel scrub sink having side walls, a bottom wall, a scrub fluid drain in the bottom wall connected to conventional fluid disposal means and a shower head connected to a source of scrub fluid via flow control valves. The scrub sink is characterized in that at least a portion of the bottom wall including the drain is perforate, a chamber below the perforate zone, a vacuum pump, conduit means connecting the low pressure side of the vacuum pump and the chamber, and further conduit means connecting the pressure side of the vacuum pump and an area remote from the scrub sink.

The invention will be more fully described in reference to the accompanying drawings.

DESCRIPTION OF THE PREFERRED EMBODIMENTS

Figure 1:
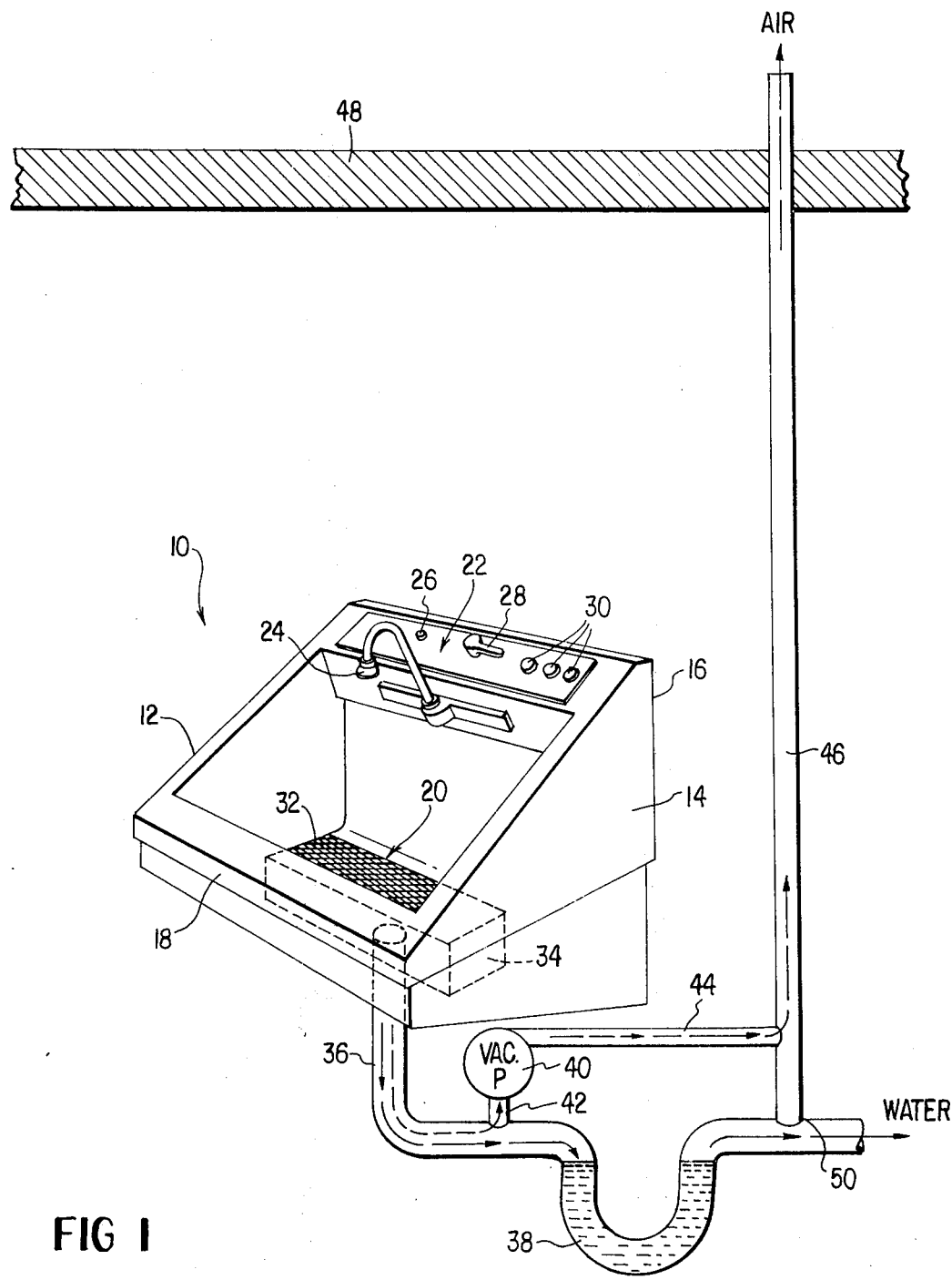
FIG. 1 is a somewhat diagrammatic partially perspective view of a scrub sink constructed in accordance with the teachings of the present invention.

Referring to FIG. 1 of the drawing, 10 generally designates a surgeon's scrub sink having side walls 12 and 14, back wall 16, front wall 18 and bottom wall generally designated 20.

The sink also includes a control panel generally designated 22 and a shower head 24. The control panel 22 may be generally of the form such as shown, for example, in the U.S. Pat. No. 3,298,037 (Luther) and includes a start button 26, a temperature control regulator 28 and various abort, short time cycle, etc., switches and pilot lights collectively designated 30.

A portion of the bottom wall 20, in a zone most likely to receive washing fluid from the shower head 24 and from the personnel scrubbing, designated 22 is perforate. The perforate section 22 is in communication with a chamber 34, the lower end of which receives a common drain and a vacuum conduit 36. The perforate portion 22 of the bottom 20 may comprise a cast or punched sheet of material which may be the same material as that employed in constructing the sink proper.

The common drain and vacuum conduit 36 is provided with a conventional trap 38 which trap communicates with a disposal sewer or the like (not shown in the drawing).

The conduit 36 also communicates with a vacuum pump 40 via conduit 42. The pressure side of the vacuum pump communicates via conduit 44 with a vent pipe 46 which, in the illustrated form of the invention, is shown communicating with the ambient atmosphere after passing through the roof or ceiling 48 of the structure within which the sink 10 is mounted. Also, as illustrated in FIG. 1, the vent pipe 46 may communicate with the common drain and vacuum line 36 downstream of the trap 38 as shown at 50.

The vacuum pump 40 is of the high capacity type and maintains a low pressure with the chamber 34 so that there is a constant inward flow of ambient air through the perforations in the perforate portion 32 of the bottom of the sink which inward flow of air carries therewith any liquid drops which may be created by the shower head 24 or drip from the body of the personnel using the scrub sink.

The motor for the high capacity pump 40 is connected to a source of electric current (not shown) via the start button 26 for the shower head 24 to insure that the vacuum system is in operation during operation of the shower.

It will be recognized by those skilled in the art that any liquid carried through the conduit 42 to the pump 40 and conduit 44 would normally drain back into the common drain and vacuum conduit at the connection of the conduit to the vent pipe 46, thus reducing to a minimum the discharge of scrubbing liquids to the atmosphere.

Figure 2:
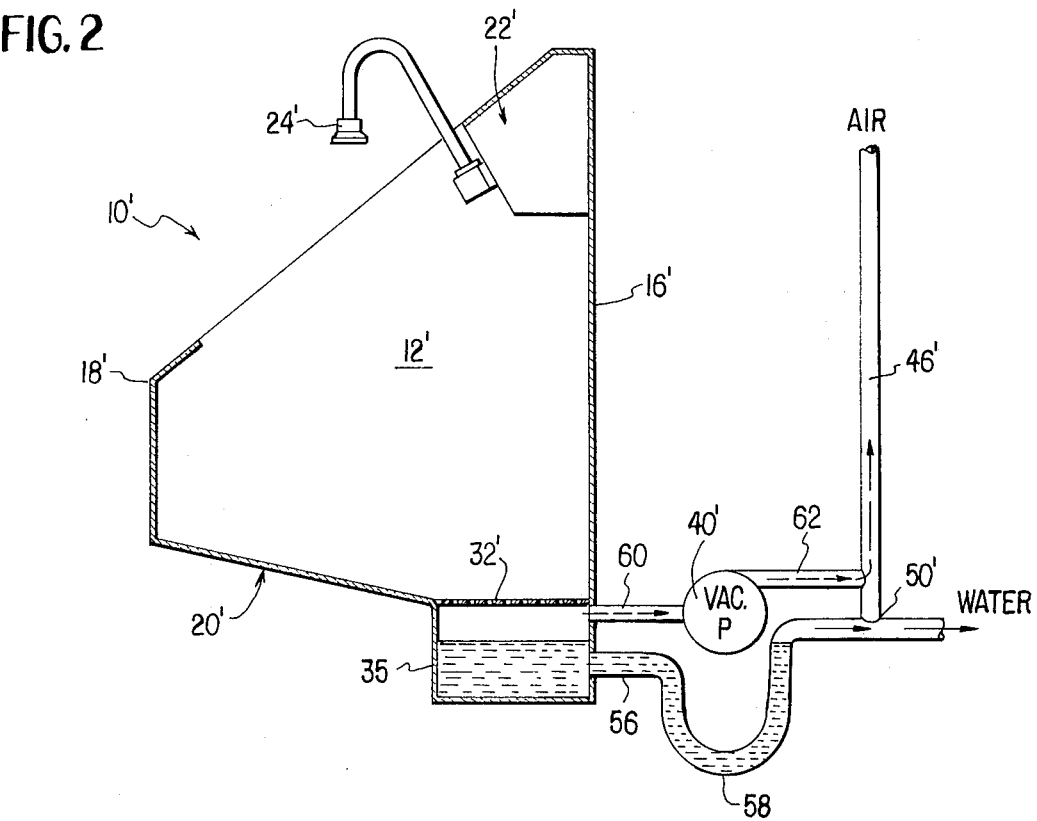
FIG. 2 is a vertical sectional view of a somewhat diagrammatic further form of the scrub sink of the present invention.

Referring now to FIG. 2 of the drawing, showing a modified form of the present invention, the reference characters employed thereon designating components like those shown in FIG. 1 are primed and 10' generally designates a scrub sink having one side wall 12', a side wall 14' (not shown), a back wall 16', a front wall 18' and a bottom wall generally designated 20'. As in the prior form of the invention, a shower head 24' is connected to a source of hot and cold water via control means 22'.

A portion 32' of the bottom 22' is perforated and communicated with a coextensive chamber 35. The chamber 35 communicates with a drain pipe 56 having a trap 58 therein. The location of the drain pipe in its communication with the chamber 35 is such that a pool of water is maintained by the trap 58 within the chamber 35. Adjacent the upper end of the chamber is a conduit 60 which communicates with a high performance vacuum pump 40'. The pressure side of the vacuum pump 40' is in communication with a conduit 62' which in turn is in communication with the vent pipe 46'. As in the prior form of the invention, the lower end of the vent pipe 46' is also in communication with the liquid drain pipe 56 downstream of the trap 58 as at 50'.

In this form of the invention, where there are separate liquid drain and vacuum connections to the chamber 35 there is less likelihood of draw-over of liquid through the vacuum connection and substantially the only liquid being drawn through the high capacity pump 40' is that suspended in the flowing air stream.

Figure 3:
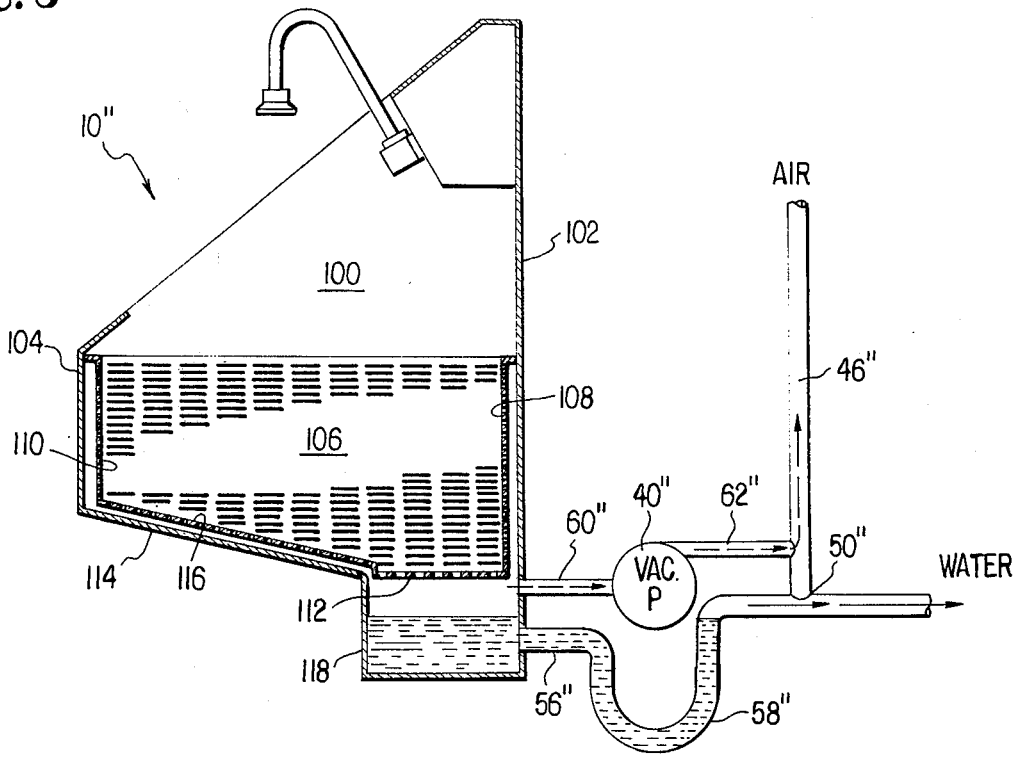
FIG. 3 is a view like FIG. 2 of a further form of the present invention.

Referring now to FIG. 3 of the drawing, a further form of the surgical scrub sink is shown and generally designated 10''. In this form of the invention, the side walls 100, back wall 102, and front wall 104 are modified such that a portion of each comprises inner wall 106, 108 and 110 respectively which inner walls are spaced from the inner surfaces of the outer sink walls 100, 102, 104 and such inner walls are perforate.

Further, in this form of the invention, in addition to the perforate section 112 the entire remaining portion of the bottom wall 114 is provided with a perforate spaced inner wall 116. As shown in FIG. 3, the space between the inner and outer side walls, back wall, front wall and bottom wall communicates with the chamber 118 positioned below the perforate portion 112 of the bottom wall so that when a reduced pressure is maintained in the chamber 118 it is also maintained in the spaces between the inner and outer side, front and back walls.

When the high capacity vacuum pump 40'' is activated to draw fluids via conduit 60' to the pump, the air and entrained liquid exits from the pump via conduit 62'' to the vent pipe 46''. Liquid draining from the sink exits from chamber 118 via drain conduit 56'' provided with a trap 58''. The air vent line 46''', as in the previous forms of the invention, is connected to the drain conduit 56'' at 50''.

In this form of the invention, the openings in bottom wall portion 112 are generally larger than the slot like openings in the inner walls 106, 108, 110 and 116 so that the major flow of ambient air and entrained particles is through the perforate bottom plate 112 thus permitting the operation of the improved scrub sink with a lower capacity vacuum pump than if the openings in the inner walls 106, 108, 110 and 116 were the same size as the openings in perforate bottom plate 112.

From the foregoing description of the preferred embodiments of the invention, it will be recognized by those skilled in the art that various modifications may be made in the illustrated structures without departing from the scope of the present invention as defined in the appended claims.

I claim:

1. A personnel scrub sink comprising sidewalls, a bottom wall, a scrub fluid drain in the bottom wall connected to conventional fluid disposal means and a shower head connected to a source of scrub fluid via flow control valves characterized in that at least a portion of the bottom wall including the drain portion is perforate, a chamber below the perforate zone, a vacuum pump, conduit means connecting the low pressure side of the vacuum pump and the chamber, and further conduit means connecting the pressure side of the vacuum pump and an area remote from the scrub sink.

2. The invention defined in claim 1 wherein said conduit means connecting the low pressure side of the vacuum pump and the chamber and the scrub sink drain comprise at least in part a common conduit.

3. The invention defined in claim 1 wherein the conduit means connecting the low pressure side of the vacuum pump and the chamber is separate from the drain for liquid from the chamber.

4. The invention defined in claim 1 wherein at least a portion of the side walls, front wall and back wall are provided with spaced perforate inner walls and the space between said inner walls and said side walls, back wall and front wall are in fluid communication with the chamber connected to the low pressure side of the vacuum pump.

5. The invention defined in claim 4 further including an inner perforate bottom wall spaced from the bottom wall and in communication with at least a portion of the bottom wall including the drain whereby the entire bottom of the scrub sink is connected to the chamber having communication with the low pressure side of the vacuum pump.

* * * * *